(12) United States Patent
Davis

(10) Patent No.: US 8,841,405 B1
(45) Date of Patent: Sep. 23, 2014

(54) THERMOSET AND THERMOPLASTIC COMPOSITIONS DERIVED FROM THE ESSENTIAL OILS OF HERBS

(71) Applicant: The United States of America as represented by the Secretary of the Navy, Washington, DC (US)

(72) Inventor: Matthew C. Davis, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/875,459

(22) Filed: May 2, 2013

Related U.S. Application Data

(60) Provisional application No. 61/647,686, filed on May 16, 2012.

(51) Int. Cl.
| | | |
|---|---|---|
| *C08G 64/00* | (2006.01) | |
| *C08G 75/20* | (2006.01) | |
| *C08G 64/16* | (2006.01) | |
| *C08G 63/685* | (2006.01) | |
| *C07C 37/14* | (2006.01) | |
| *C08G 73/10* | (2006.01) | |
| *C08G 71/04* | (2006.01) | |
| *C08G 65/40* | (2006.01) | |
| *C08G 63/02* | (2006.01) | |

(52) U.S. Cl.
CPC ............ *C08G 75/20* (2013.01); *C08G 64/1608* (2013.01); *C08G 63/685* (2013.01); *C07C 37/14* (2013.01); *C08G 73/10* (2013.01); *C08G 71/04* (2013.01); *C08G 65/4018* (2013.01)
USPC .......................................... 528/196; 528/198

(58) Field of Classification Search
CPC ..................................................... C08G 64/045
USPC ................................................... 528/196, 198
See application file for complete search history.

(56) References Cited

U.S. PATENT DOCUMENTS

| | | |
|---|---|---|
| 3,922,368 A | 11/1975 | Klaul et al. |
| 5,260,398 A | 11/1993 | Liao et al. |
| 5,406,003 A | 4/1995 | Wang et al. |
| 7,439,353 B2 | 10/2008 | Matsuo et al. |
| 7,825,169 B2 | 11/2010 | Wada et al. |
| 2002/0058778 A1 | 5/2002 | Konarski et al. |
| 2012/0165429 A1 | 6/2012 | Boulevin et al. |

FOREIGN PATENT DOCUMENTS

| | | |
|---|---|---|
| EP | 2167478 | 3/2010 |
| JP | 01290642 | 11/1989 |
| WO | WO 0055123 | 9/2000 |

OTHER PUBLICATIONS

High Tg thermosetting resins from resveratrol Poly. Chem.(2013), 4(13), 3859-3865 CODEN:PCOHC2; ISSN: 1759-9962; Eng.Rec. 4th Apr. 2013, Acc.d 25th Apr. 20 examiner has copy.

*Primary Examiner* — Terressa Boykin

(74) *Attorney, Agent, or Firm* — James M. Saunders; Charlene A. Haley

(57) ABSTRACT

A process, thermoset resin, and thermoplastic structures from renewable chemical feedstocks derived from the essential oils from herbs and other plants. The processes for making diphenol products including extracting isomers of 4-methoxyphenylpropene from plant sources, transforming isomers by olefin cross or self-cross olefin metathesis and at least one catalyst to produce dimeric structures having two equivalents of protected phenolic groups, and deprotecting methyl ethers to yield diphenolic products.

15 Claims, No Drawings

THERMOSET AND THERMOPLASTIC COMPOSITIONS DERIVED FROM THE ESSENTIAL OILS OF HERBS

CROSS-REFERENCE TO RELATED APPLICATIONS

This is a non-provisional patent application, claiming the benefit of, parent application Ser. No. 61/647,686 filed on May 16, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to renewable feedstocks, and more particularly, to renewable chemical feedstocks derived from the essential oils from herbs and other plants.

DESCRIPTION OF EMBODIMENTS OF THE INVENTION

Thermosetting resins are uncured and at room temperature they are in a liquid state. Thermosetting resins can exhibit properties including: great adhesion, great finishing as in polishing and painting, resistance to solvents and corrosives, resistance to heat and high temperature, fatigue strength, and tailored elasticity. In a thermoset resin, the raw uncured resin molecules are crossed linked through a catalytic chemical reaction. Through this chemical reaction, most often exothermic, the resin creates extremely strong bonds to one another, and the resin changes state from a liquid to a solid. A thermosetting resin, once catalyzed, it cannot be reversed or reformed. Meaning, once a thermoset composite is formed, it cannot be remolded or reshaped. Because of this, the recycling of thermoset composites is extremely difficult. The thermoset resin itself is not recyclable, however, there are a few new companies who have successfully removed the resin through pyrolization and are able to reclaim the reinforcing fiber. Thermoplastic resins are most commonly unreinforced, meaning, the resin is formed into shapes and have no reinforcement providing strength. Many thermoplastic products use short discontinuous fibers as a reinforcement. There are two major advantages of thermoplastic composites. The first is that many thermoplastic resins have an increased impact resistance to comparable thermoset composites. In some instances, the difference is as high as 10 times the impact resistance. An advantage of thermoplastic composites is the ability reform and thermoplastic composites, at room temperature, are in a solid state. When heat and pressure impregnate a reinforcing fiber, a physical change occurs; not a chemical reaction as with a thermoset. This allows thermoplastic composites to be reformed and reshaped. (Thermoplastic vs Thermoset Resins from about.com)

In embodiments of the invention, thermosets can be conveniently prepared from the extracts from the essential oils mainly from herbs and other plants. The prepared products can be polymerized or cured into materials with high heat resistance. Decreased reliance on petrochemicals is realized. Applications include aerospace uses requiring high strength-to-weight ratios because the novel materials are lightweight and thermally resistant.

The Navy and Department of Defense (DoD) are heavily dependent on petroleum for sources of mission-critical composite materials. Embodiments of the invention address this issue by employing readily essential oils from plants to make new composite materials. The composite materials may find uses in aerospace applications. The essential oil products from plants represent a renewable resource for resins and plastics.

There are many plants, especially herbs, which provide essential oils when extracted. In particular tarragon (*Artemisia dracunculus*) and star anise (*Illicium verum*) yield essential oils that are almost exclusively the isomers of 4-methoxyphenylpropene (estragole and anethole). These products transform by the reaction known as olefin metathesis (Chemical Schematic 1) to give new products that are dimeric in structure having two equivalents of protected phenolic groups in the molecule. The catalyst to carry out this transformation is commercially available to those skilled in the art. The formed point of unsaturation can be reduced or not and then the methyl ethers can be deprotected to yield the new diphenolic products. The diphenolic products from natural and renewable sources can then be inserted into the many known polymerization reactions (Chemical Schematic 2) to those skilled in the art including, but not limited to, polyesters, polycarbonates, polycyanurates, polyurethanes, polyetherimides, polyetheretherketones, and polysulfones.

Chemical Schematic 1 is an example derivation of essential oils from tarragon and star anise to prepare diphenol(s) building blocks.

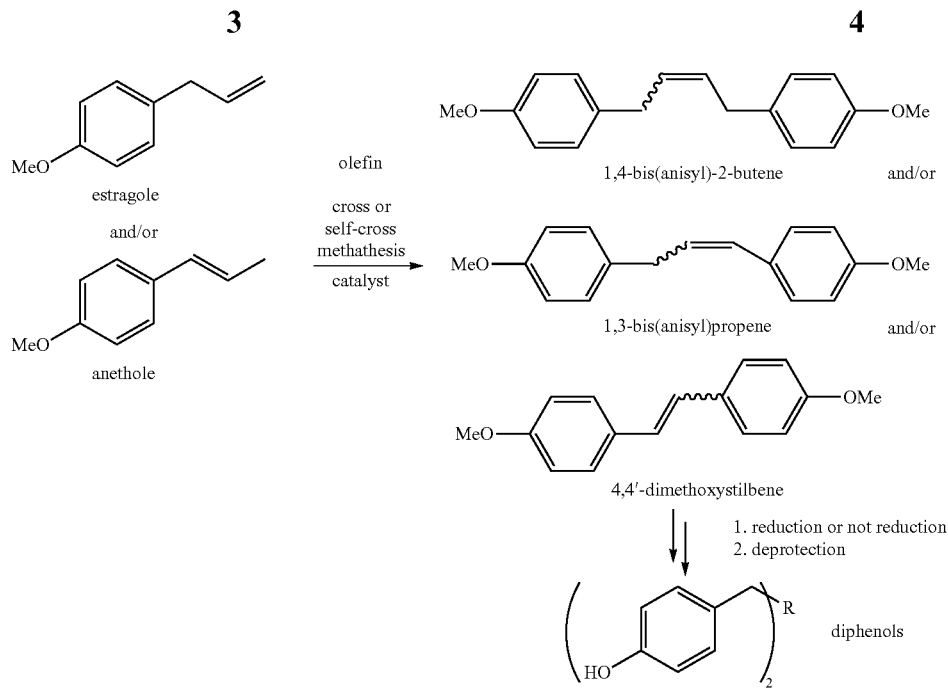

Chemical Schematic 2 is an example of polymerization possibilities of plant derived monomers.

Scheme 3:

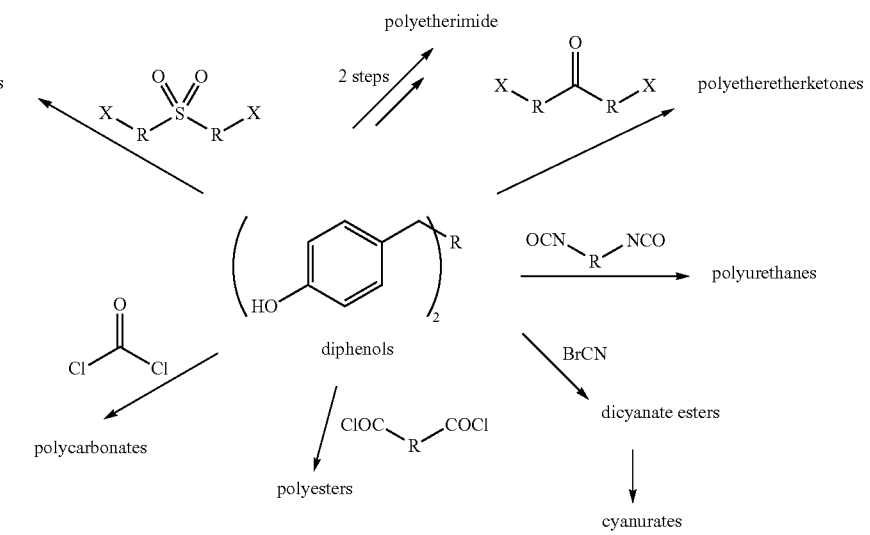

In addition, trans-anethole can be dimerized into two different dimers, one di-cyclic and the other tricyclic, by a variety of different acid catalyst (Scheme 3). The resulting diphenols of these dimers possess significantly different properties which will also affect the resulting polymers made thereof. The tricyclic dimer will give a polymer with a higher Tg and the linear dimer will have lower Tg. These two products can be useful for creating polymers of dialed thermal characteristics which may be important for processes under which the polymers will be fashioned into components of Navy interests.

There are also some embodiments for co-polymerization using sequential or mixed additions to the phenolic compounds.

Dimerization of trans-anethole into linear or tricyclic diphenols.

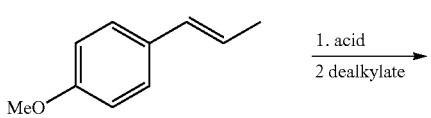

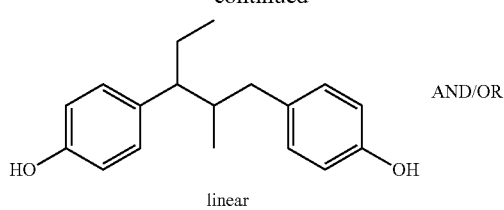

linear

AND/OR

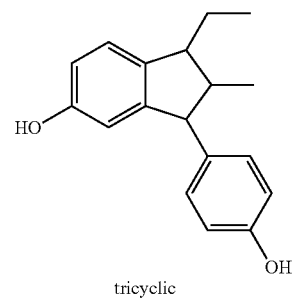

tricyclic

Embodiments of the invention generally relate to processes for making diphenol products including, extracting isomers of 4-methoxyphenylpropene from plant sources, transforming the isomers by olefin cross or self-cross olefin metathesis and at least one catalyst to produce dimeric structures having two equivalents of protected phenolic groups, and deprotecting methyl ethers to yield diphenolic products. Embodiments of the invention further include polymerizing the diphenol products with heat to produce thermoset resins. Other embodiments further include polymerizing the diphenol products with heat to produce thermoplastics. Other embodiments further include polymerizing the diphenol products with

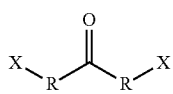

and heat, wherein R includes a benzene ring and X includes a fluorine or chlorine to produce polyetheretherketones.

Yet other embodiments further include polymerizing the diphenol products with

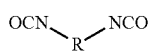

and heat, wherein R comprises a benzene ring to produce polyurethanes. Still yet other embodiments further include polymerizing the diphenol products with

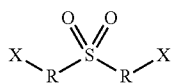

and heat, wherein R includes a benzene ring and X includes a fluorine or chlorine to produce polysulfones. Yet other embodiments further include polymerizing the diphenol products with

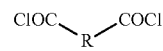

and heat, wherein R includes a benzene ring to produce polyesters. Other embodiments further include polymerizing the diphenol products by reacting two equivalents of 4-fluorophthalic anhydride forming a bis-anhydride, condensation polymerizing the bis-anhydride with an aromatic diamine producing polyetherimides.

In embodiments, the aromatic diamine includes, but is not limited to, 1,3-phenylenediamine. Other embodiments further include polymerizing the diphenol products with

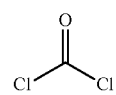

and heat to produce polycarbonates. Yet other embodiments further include polymerizing the diphenol products with BrCN and heat to produce dicyanate esters. Other embodiments further include polymerizing said dicyanate esters with heat to produce cyanurates. While other embodiments further include a catalyst with heat to produce cyanurates.

Other aspects of the invention include the thermoset resins and thermoplastics produced by the processes and methods herein.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for making diphenol products, comprising:
   extracting isomers of 4-methoxyphenylpropene from plant sources;
   transforming said isomers by olefin cross or self-cross olefin metathesis and at least one catalyst to produce dimeric structures having two equivalents of protected phenolic groups; and
   deprotecting methyl ethers to yield diphenolic products.

2. The process according to claim 1, further comprising polymerizing said diphenol products with heat to produce thermoset resins.

3. The process according to claim 1, further comprising polymerizing said diphenol products with heat to produce thermoplastics.

4. The process according to claim 1, further comprising polymerizing said diphenol products with

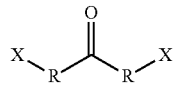

and heat, wherein R comprises a benzene ring and X comprises a fluorine or chlorine to produce polyetheretherketones.

5. The process according to claim 1, further comprising polymerizing said diphenol products with

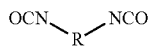

and heat, wherein R comprises a benzene ring to produce polyurethanes.

6. The process according to claim 1, further comprising polymerizing said diphenol products with

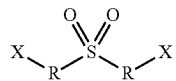

and heat, wherein R comprises a benzene ring and X comprises a fluorine or chlorine to produce polysulfones.

7. The process according to claim 1, further comprising polymerizing said diphenol products with

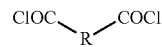

and heat, wherein R comprises a benzene ring to produce polyesters.

8. The process according to claim 1, further comprising polymerizing said diphenol products by reacting two equivalents of 4-fluorophthalic anhydride forming a bis-anhydride, condensation polymerizing said bis-anhydride with an aromatic diamine producing polyetherimides.

9. The process according to claim 8, wherein said aromatic diamine comprises 1,3-phenylenediamine.

10. The process according to claim 1, further comprising polymerizing said diphenol products with

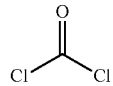

and heat to produce polycarbonates.

11. The process according to claim 1, further comprising polymerizing said diphenol products with BrCN and heat to produce dicyanate esters.

12. The process according to claim 11, further comprising further polymerizing said dicyanate esters with heat to produce cyanurates.

13. The process according to claim 12, further comprising a catalyst with said heat to produce cyanurates.

14. Thermoset resins produced by the processes in claim 2.

15. Thermoplastics produced by the processes in claim 3.

* * * * *